United States Patent
Morita

(10) Patent No.: US 11,134,909 B2
(45) Date of Patent: Oct. 5, 2021

(54) IMAGE PROCESSING APPARATUS, IMAGE PROCESSING METHOD, AND IMAGE PROCESSING PROGRAM

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 89 days.

(21) Appl. No.: 16/439,709

(22) Filed: Jun. 13, 2019

(65) Prior Publication Data

US 2019/0388046 A1 Dec. 26, 2019

(30) Foreign Application Priority Data

Jun. 26, 2018 (JP) .............................. JP2018-121078

(51) Int. Cl.
| | |
|---|---|
| *A61B 6/00* | (2006.01) |
| *A61B 6/04* | (2006.01) |
| *G06T 7/00* | (2017.01) |

(52) U.S. Cl.
CPC ............ *A61B 6/502* (2013.01); *A61B 6/0414* (2013.01); *A61B 6/5217* (2013.01);
(Continued)

(58) Field of Classification Search
CPC ..... A61B 6/0414; A61B 6/502; A61B 6/5205; A61B 6/5217; G06T 7/0012; G06T 2207/10116; G06T 2207/30068
See application file for complete search history.

(56) References Cited

U.S. PATENT DOCUMENTS

| | | | |
|---|---|---|---|
| 2009/0252396 A1* | 10/2009 | Morita .................... | G06T 5/008 382/132 |
| 2010/0246924 A1* | 9/2010 | Morita ................. | A61B 5/4872 382/132 |

(Continued)

FOREIGN PATENT DOCUMENTS

| | | |
|---|---|---|
| JP | 2009-247521 A | 10/2009 |
| JP | 2010-253245 A | 11/2010 |

(Continued)

OTHER PUBLICATIONS

Holland et al. "Optimization of volumetric breast density estimation in digital mammograms." Physics in Medicine & Biology 62.9 (2017): 3779. (Year: 2017).*

(Continued)

*Primary Examiner* — Katrina R Fujita
(74) *Attorney, Agent, or Firm* — Solaris Intellectual Property Group, PLLC

(57) ABSTRACT

An image processing apparatus includes: an acquisition unit that acquires a plurality of radiographic images of the same breast which have captured in a plurality of different states related to compression of the breast; and a derivation unit that derives, on the basis of an amount of incident radiation derived from a value of a fat tissue pixel in a radiographic image in which the fat tissue pixel obtained by a portion of the breast which is estimated to be composed of only fat tissues is included in a breast image among the plurality of radiographic images acquired by the acquisition unit, a percentage of mammary glands of a breast image in a radiographic image different from the radiographic image used to derive the amount of incident radiation.

12 Claims, 9 Drawing Sheets

(52) U.S. Cl.
    CPC .. *G06T 7/0012* (2013.01); *G06T 2207/10116* (2013.01); *G06T 2207/30068* (2013.01)

(56) References Cited

U.S. PATENT DOCUMENTS

| | | | |
|---|---|---|---|
| 2011/0026791 A1 | 2/2011 | Collins et al. | |
| 2014/0010429 A1 | 1/2014 | Highnam et al. | |
| 2016/0133033 A1* | 5/2016 | Highnam | G06T 11/005 382/131 |
| 2016/0292851 A1 | 10/2016 | Shin | |
| 2017/0116731 A1* | 4/2017 | Tsunomori | G06T 7/136 |

FOREIGN PATENT DOCUMENTS

| | | | |
|---|---|---|---|
| JP | 2016-158963 A | 9/2016 |
| JP | 2016-190012 A | 11/2016 |

OTHER PUBLICATIONS

Van Engeland, S. et al, "Volumetric Breast Density Estimation from Full-field Digital Mammograms", IEEE Transactions on Medical Imaging, IEEE Service Center, Piscataway, NY, US, vol. 25, No. 3, Mar. 1, 2006, p. 273-282.

Extended European Search Report dated Nov. 12, 2019, issued in corresponding EP Patent Application No. 19180945.8.

English language translation of the following: Office action dated Jun. 29, 2021 from the JPO in a Japanese patent application No. 2018-121078 corresponding to the instant patent application. This office action translation is submitted now in order to supplement the understanding of the cited references which are being disclosed in the instant Information Disclosure Statement.

\* cited by examiner

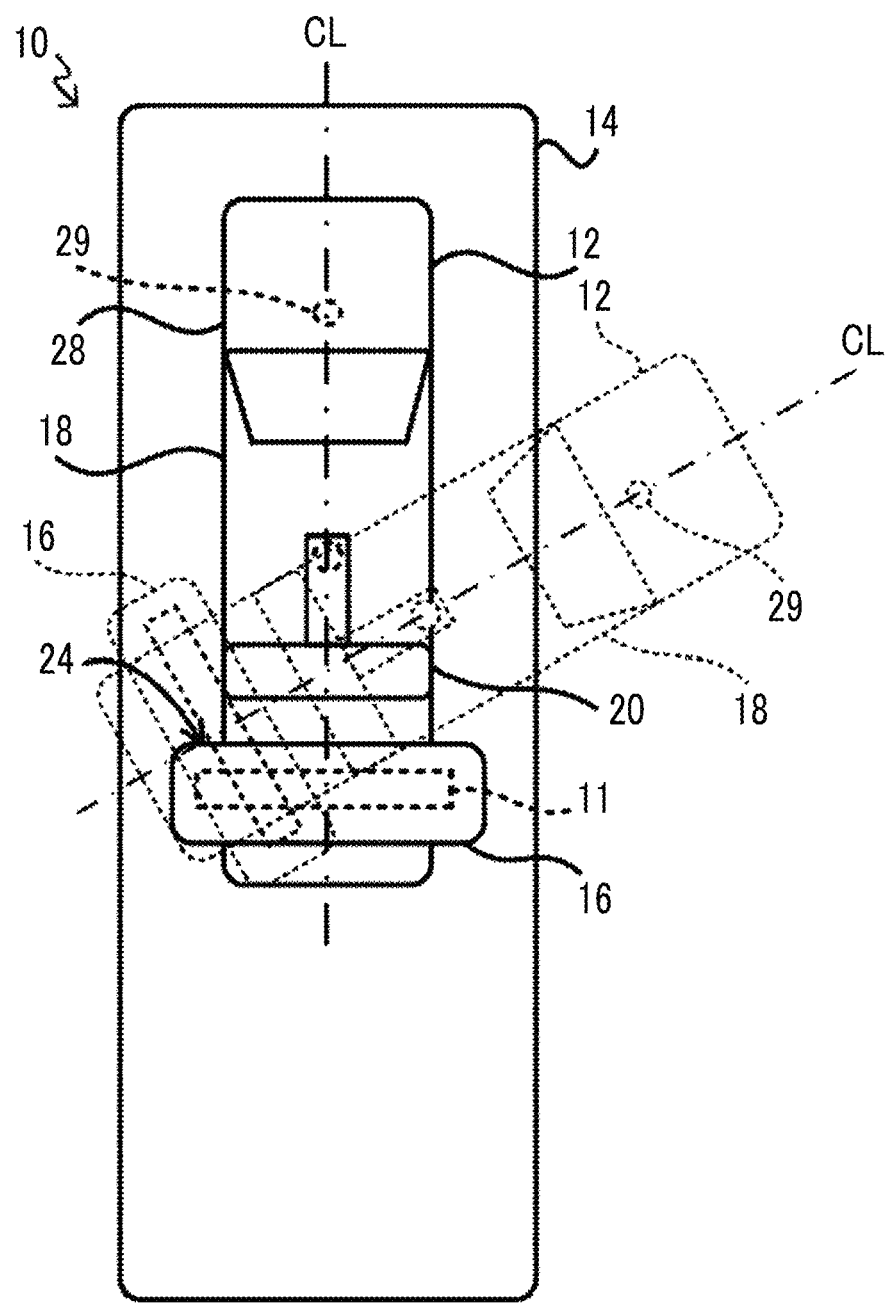

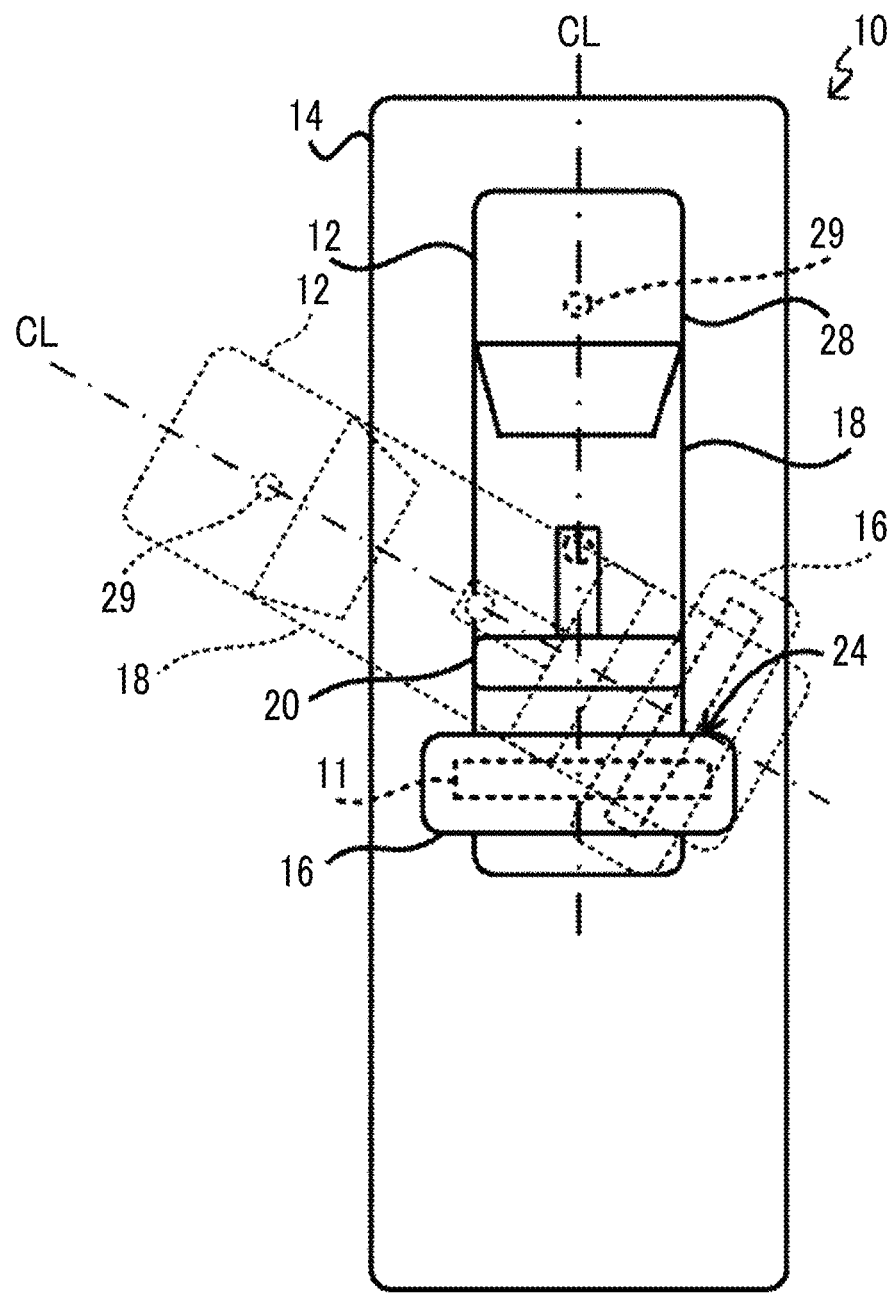

IMAGE PROCESSING APPARATUS, IMAGE PROCESSING METHOD, AND IMAGE PROCESSING PROGRAM

CROSS-REFERENCE TO RELATED APPLICATION

This application claims priority under 35 USC 119 from Japanese Patent Application No. 2018-121078 filed Jun. 26, 2018, the disclosure of which is incorporated by reference herein.

BACKGROUND

Technical Field

The present disclosure relates to an image processing apparatus, an image processing method, and an image processing program.

Related Art

In general, an object of interest, such as a breast cancer, in the breast has been diagnosed on the basis of a radiographic image of the breast of a subject captured by a so-called mammography apparatus. However, in the case of the breast with a high percentage of mammary glands, an image of the object of interest in the radiographic image may be hidden by the mammary glands and may be difficult to see. Therefore, a technique has been known which derives the percentage of the mammary glands. For example, JP2010-253245A discloses a technique that estimates a fat image obtained in a case in which the entire breast is assumed to be composed of only the fat tissues and derives the percentage of the mammary glands, using the pixel value of the fat image and an attenuation coefficient of radiation.

SUMMARY

In the technique disclosed in JP2010-253245A, the value of a fat tissue pixel obtained by a portion of the breast which is estimated to be composed of only the fat tissues in the radiographic image is used. However, for example, in some cases, the fat tissue pixel is not included in the radiographic image according to the compressed state of the breast which varies depending on an imaging direction. In this case, there is room for improvement in the technique disclosed in JP2010-253245A.

The present disclosure has been made in view of the above-mentioned problems and an object of the present disclosure is to provide an image processing apparatus, an image processing method, and an image processing program that can derive the percentage of the mammary glands with high accuracy even in a case in which a fat tissue pixel obtained by a portion of the breast which is estimated to be composed of only fat tissues is not included in a radiographic image of the breast.

In order to achieve the object, according to a first aspect of the present disclosure, there is provided an image processing apparatus comprising: an acquisition unit that acquires a plurality of radiographic images of the same breast which have captured in a plurality of different states related to compression of the breast; and a derivation unit that derives, on the basis of an amount of incident radiation derived from a value of a fat tissue pixel in a radiographic image in which the fat tissue pixel obtained by a portion of the breast which is estimated to be composed of only fat tissues is included in a breast image among the plurality of radiographic images acquired by the acquisition unit, a percentage of mammary glands of a breast image in a radiographic image different from the radiographic image used to derive the amount of incident radiation.

According to a second aspect of the present disclosure, in the image processing apparatus according to the first aspect, the derivation unit may derive the percentage of the mammary glands for each pixel.

According to a third aspect of the present disclosure, in the image processing apparatus according to the first or second aspect, the plurality of radiographic images may include a plurality of radiographic images in which compression directions of the breast are different from each other.

According to a fourth aspect of the present disclosure, in the image processing apparatus according to the first or second aspect, the plurality of radiographic images may include a radiographic image captured in a craniocaudal direction and a radiographic image captured in a mediolateral-oblique direction.

According to a fifth aspect of the present disclosure, in the image processing apparatus according to any one of the first to fourth aspects, the acquisition unit may further acquire information indicating a thickness of each breast in the capture of the plurality of radiographic images and the derivation unit may derive the percentage of the mammary glands on the basis of a difference between the thicknesses of the breast.

According to a sixth aspect of the present disclosure, in the image processing apparatus according to any one of the first to fourth aspects, the derivation unit may derive the percentage of the mammary glands on the basis of a ratio of an amount of incident radiation derived on the basis of a pixel value of a direct region corresponding to radiation which is directly emitted without passing through the breast in the radiographic image including the fat tissue pixel and an amount of incident radiation derived on the basis of a pixel value of a direct region corresponding to radiation which is directly emitted without passing through the breast in the radiographic image different from the radiographic image used to derive the amount of incident radiation.

According to a seventh aspect of the present disclosure, in the image processing apparatus according to any one of the first to sixth aspects, in a case in which the plurality of radiographic images do not include the radiographic image including the fat tissue pixel, the derivation unit may derive the percentage of the mammary glands on the basis of a value of a mammary gland tissue pixel obtained by a portion of the breast which is estimated to be composed of only mammary gland tissues.

According to an eighth aspect of the present disclosure, the image processing apparatus according to any one of the first to sixth aspects may further comprise a determination unit that determines a type of the breast on the basis of the plurality of radiographic images. In a case in which the type of the breast determined by the determination unit is a type predetermined to be a breast with a relatively high mammary gland density, the derivation unit may derive the percentage of the mammary glands on the basis of a value of a mammary gland tissue pixel obtained by a portion of the breast which is estimated to be composed of only mammary gland tissues.

According to a ninth aspect of the present disclosure, there is provided an image processing method comprising: acquiring a plurality of radiographic images of the same breast which have captured in a plurality of different states related to compression of the breast; and deriving, on the basis of an amount of incident radiation derived from a value of a fat tissue pixel in a radiographic image in which the fat tissue pixel obtained by a portion of the breast which is estimated to be composed of only fat tissues is included in a breast image among the acquired plurality of radiographic images, a percentage of mammary glands of a breast image in a radiographic image different from the radiographic image used to derive the amount of incident radiation.

According to a tenth aspect of the present disclosure, there is provided an image processing program that causes a computer to perform: acquiring a plurality of radiographic images of the same breast which have captured in a plurality of different states related to compression of the breast; and deriving, on the basis of an amount of incident radiation derived from a value of a fat tissue pixel in a radiographic image in which the fat tissue pixel obtained by a portion of the breast which is estimated to be composed of only fat tissues is included in a breast image among the acquired plurality of radiographic images, a percentage of mammary glands of a breast image in a radiographic image different from the radiographic image used to derive the amount of incident radiation.

According to the present disclosure, it is possible to derive the percentage of the mammary glands with high accuracy even in a case in which a fat tissue pixel obtained by a portion of the breast which is estimated to be composed of only fat tissues is not included in a radiographic image of the breast.

BRIEF DESCRIPTION OF THE DRAWINGS

Exemplary Embodiments of the present invention will be described in detail with reference to the following figures, wherein:

FIG. 3A is a front view illustrating an example of the state of the mammography apparatus in a case in which an image of the left breast of a subject is captured.

FIG. 3B is a front view illustrating an example of the state of the mammography apparatus in a case in which an image of the right breast of the subject is captured.

DETAILED DESCRIPTION

Hereinafter, embodiments of the invention will be described in detail with reference to the drawings. The embodiments do not limit the invention.

Figure 1:
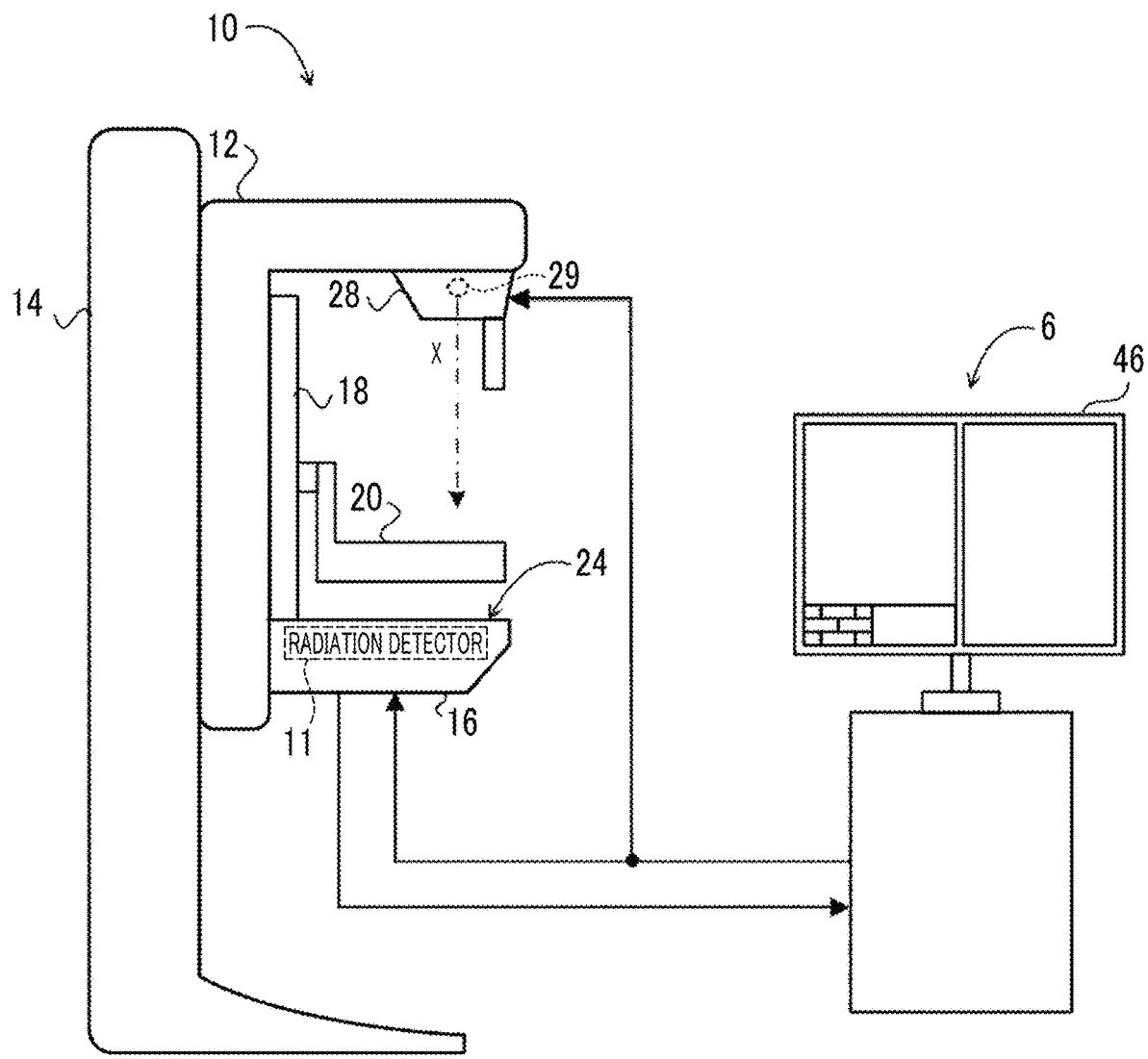
FIG. 1 is a diagram illustrating an example of the overall configuration of a radiography system according to an embodiment.

First, an example of the overall configuration of a radiography system according to this embodiment will be described. FIG. 1 is a configuration diagram illustrating an example of the overall configuration of a radiography system 1 according to this embodiment.

The radiography system 1 according to this embodiment has a function of capturing radiographic images in response to an operation of a user, such as a doctor or a radiology technician, on the basis of a command (imaging order) input from an external system (for example, a radiology information system (RIS)) through a console 6.

Figure 2:
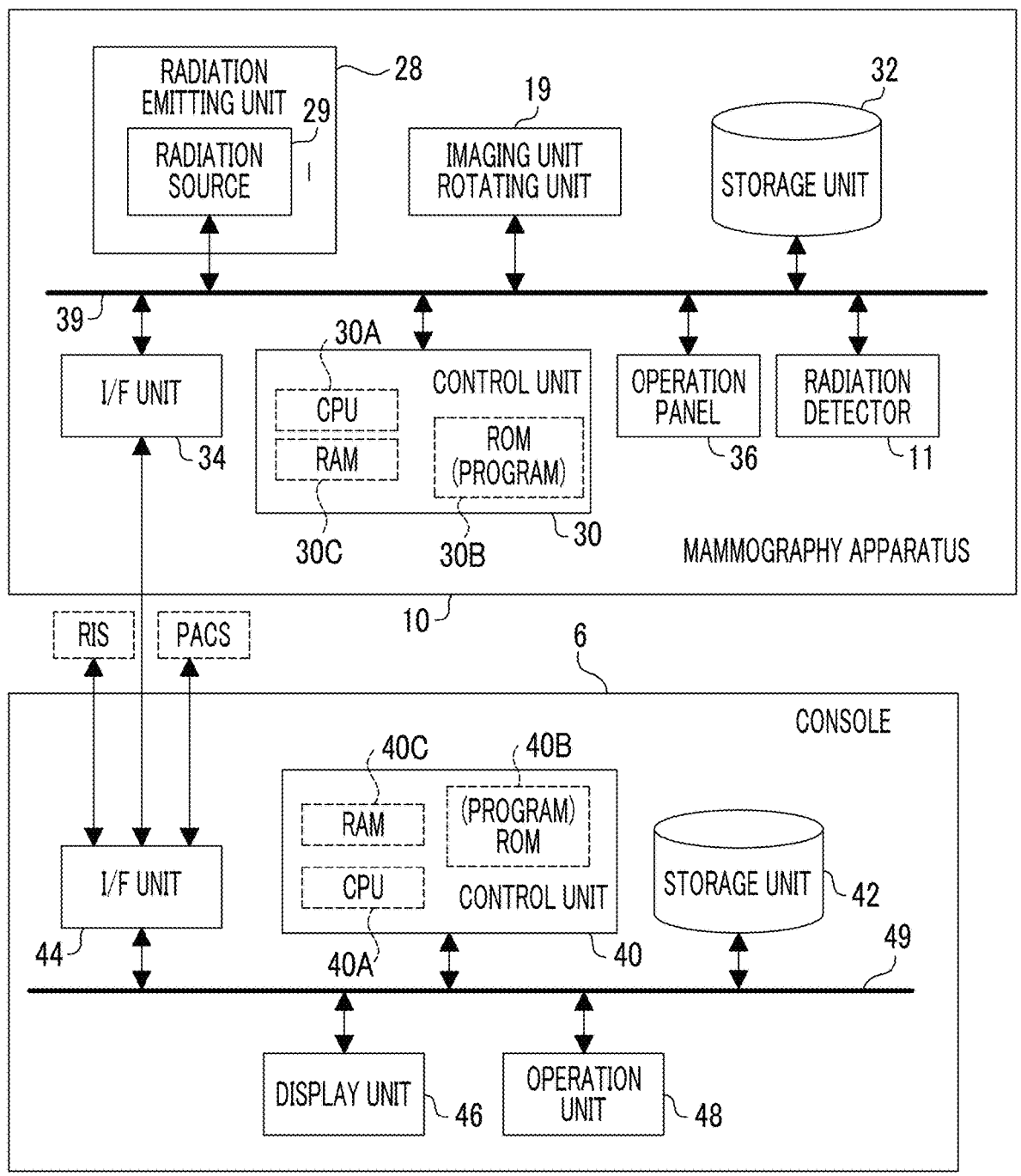
FIG. 2 is a block diagram illustrating an example of the configuration of a console and a mammography apparatus according to the embodiment.

As illustrated in FIG. 1, the radiography system 1 according to this embodiment comprises the console 6 and a mammography apparatus 10. FIG. 2 is a block diagram illustrating an example of the configuration of the console 6 and the mammography apparatus 10 according to this embodiment.

The console 6 according to this embodiment has a function of controlling the mammography apparatus 10 using, for example, an imaging order or various kinds of information acquired from an external system through a wireless communication local area network (LAN). The console 6 according to this embodiment is an example of an image processing apparatus according to the present disclosure.

For example, the console 6 according to this embodiment is a server computer. As illustrated in FIG. 2, the console 6 includes a control unit 40, a storage unit 42, an interface (I/F) unit 44, a display unit 46, and an operation unit 48. The control unit 40, the storage unit 42, the I/F unit 44, the display unit 46, and the operation unit 48 are connected to each other through a bus 49, such as a system bus or a control bus, such that they can transmit and receive various kinds of information.

The control unit 40 according to this embodiment controls the overall operation of the console 6. The control unit 40 according to this embodiment includes a central processing unit (CPU) 40A, a read only memory (ROM) 40B, and a random access memory (RAM) 40C. For example, various programs including a mammary gland percentage derivation processing program (which will be described below) executed by the CPU 40A are stored in the ROM 40B in advance. The RAM 40C temporarily stores various kinds of data.

For example, the image data of a radiographic image captured by the mammography apparatus 10 and various other kinds of information are stored in the storage unit 42. Examples of the storage unit 42 include a hard disk drive (HDD) and a solid state drive (SSD). The I/F unit 44 transmits and receives various kinds of information to and from the mammography apparatus 10 or external systems, such as an RIS and a picture archiving and communication system (PACS), using at least one of wireless communication or wired communication.

The display unit 46 displays, for example, information related to imaging and the captured radiographic image. The operation unit 48 is used by a user to input, for example, a command to capture a radiographic image and a command related to image processing for the captured radiographic image. For example, the operation unit 48 may have the form of a keyboard or various types of switches or the form of a touch panel integrated with the display unit 46.

The mammography apparatus 10 according to this embodiment is an apparatus that irradiates the breast of a subject, which is an object, with radiation X (X-rays) to capture the radiographic image of the breast. As illustrated in FIG. 1, the mammography apparatus 10 comprises an imaging unit 12 and a base portion 14 that supports the imaging unit 12.

The imaging unit 12 comprises an imaging table 16 having a planar imaging surface 24 that come into contact with the breast of the subject, a compression plate 20 that compresses the breast against the imaging surface 24 of the imaging table 16, and a holding portion 18 that supports the imaging table 16 and the compression plate 20. In addition, a member that transmits the radiation X is used as the compression plate 20. In addition, the imaging unit 12 according to this embodiment is rotated by an imaging unit rotating unit 19 in a state in which the imaging unit 12 holds the imaging table 16, which will be described in detail below.

The holding portion 18 supports the imaging table 16 and a radiation source 29 such that the imaging surface 24 and the radiation source 29 are separated by a predetermined distance. In addition, the holding portion 18 holds the compression plate 20 such that the compression plate 20 is slid to change the distance between the compression plate 20 and the imaging surface 24.

In a case in which the mammography apparatus 10 captures the radiographic image of the breast of the subject, for example, a user positions the subject and the breast placed on the imaging surface 24 of the imaging table 16 is compressed between the compression plate 20 and the imaging surface 24 and is fixed.

A radiation detector 11 that detects the radiation X transmitted through the breast and the imaging surface 24 is provided in the imaging table 16. A radiographic image is generated on the basis of the radiation X detected by the radiation detector 11. However, the type of radiation detector 11 according to this embodiment is not particularly limited. For example, the radiation detector 11 may be an indirect-conversion-type radiation detector that converts the radiation X into light and converts the converted light into charge or a direct-conversion-type radiation detector that directly converts the radiation X into charge. In this embodiment, image data indicating the radiographic image output from the radiation detector 11 of the mammography apparatus 10 is transmitted to the console 6.

The mammography apparatus 10 according to this embodiment can perform both craniocaudal (CC) imaging in which an imaging direction is a craniocaudal direction and mediolateral-oblique (MLO) imaging in which the imaging direction is a mediolateral-oblique direction for the breast. In the following description, in radiography, the position of the radiation source 29 in a case in which the radiation source 29 emits the radiation X to the imaging table 16 is referred to as an "imaging position".

In a case in which the CC imaging is performed, the imaging table 16 is adjusted to a state in which the imaging surface 24 faces the upper side (the head of the subject) of the mammography apparatus 10, that is, a state in which a normal direction to the imaging surface 24 is vertical. In this case, the position of the radiation source 29 is adjusted to an imaging position where the radiation source 29 faces the imaging surface 24 of the imaging table 16. Specifically, the position of the radiation source 29 is adjusted to an imaging position where the radiation source 29 is vertical with respect to a normal line CL (see FIGS. 3A and 3B) to the imaging surface 24 (that is, the angle formed between the normal line CL (see FIGS. 3A and 3B) and the radiation source 29 is 0 degrees). Therefore, the radiation X is emitted from the radiation source 29 to the breast in a direction from the head to the foot of the subject and the CC imaging is performed.

In a case in which the MLO imaging is performed, the imaging unit rotating unit 19 adjusts the position of the imaging table 16 to a state in which the imaging surface 24 is rotated to a predetermined angle in the range that is equal to or greater than 45 degrees and less than 90 degrees, as compared to the case in which the CC imaging is performed. Specifically, in a case in which the image of the left breast of the subject is captured, for example, as represented by a dashed line in FIG. 3A, the imaging unit rotating unit 19 rotates the imaging table 16 such that the imaging surface 24 is inclined to the right. In addition, the image of the right breast of the subject is captured, as represented by a dashed line in FIG. 3B, the imaging unit rotating unit 19 rotates the imaging table 16 such that the imaging surface 24 is inclined to the left. Then, the position of the radiation source 29 is adjusted to an imaging position where the radiation source 29 faces the imaging surface 24 of the imaging table 16. Therefore, the radiation X is emitted from the radiation source 29 to the breast in a direction from the center to the outside of the body of the subject (from a part between the breasts to the arm of the subject) and the MLO imaging is performed.

As such, in the mammography apparatus 10 according to this embodiment, in both the CC imaging and the MLO imaging, the radiation source 29 faces the imaging surface 24 at the imaging position. Hereinafter, a radiographic image obtained by the CC imaging is referred to as a "CC image" and a radiographic image obtained by the MLO imaging is referred to as an "MLO image". In addition, in a case in which the CC image and the MLO images are generically referred to, they are simply referred to as "radiographic images".

As illustrated in FIG. 2, the mammography apparatus 10 according to this embodiment comprises the radiation detector 11, the imaging unit rotating unit 19, a radiation emitting unit 28 including the radiation source 29, a control unit 30, a storage unit 32, an I/F unit 34, and an operation panel 36. The radiation detector 11, the imaging unit rotating unit 19, the radiation emitting unit 28, the control unit 30, the storage unit 32, the I/F unit 34, and the operation panel 36 are connected to each other through a bus 39, such as a system bus or a control bus, such that they can transmit and receive various kinds of information.

The control unit 30 according to this embodiment controls the overall operation of the mammography apparatus 10. In addition, in a case in which a radiographic image is captured, the control unit 30 according to this embodiment controls the radiation detector 11 and the radiation emitting unit 28. The control unit 30 according to this embodiment comprises a CPU 30A, a ROM 30B, and a RAM 30C. For example, various programs including a program for controlling the capture of a radiographic image which are executed by the CPU 30A are stored in the ROM 30B in advance. The RAM 30C temporarily stores various kinds of data.

For example, the image data of the radiographic image captured by the radiation detector 11 and various other kinds of information are stored in the storage unit 32. Examples of the storage unit 32 include an HDD and an SSD. The I/F unit 34 transmits and receives various kinds of information to and from the console 6 using wireless communication or wired communication. For example, the operation panel 36 is provided as a plurality of switches in the imaging table 16 of the mammography apparatus 10. In addition, the operation panel 36 may be provided as a touch panel.

Figure 4:
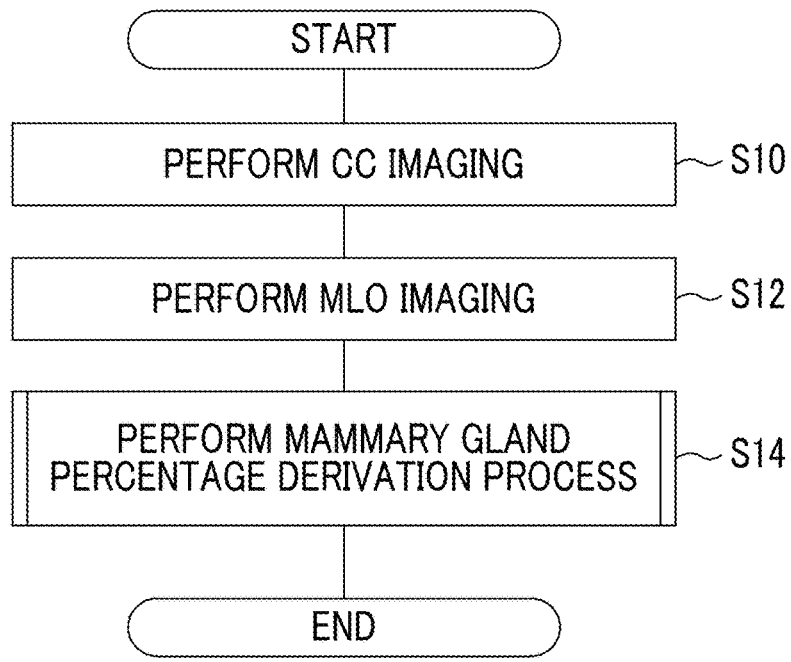
FIG. 4 is a flowchart illustrating an example of the flow of an imaging operation of capturing a radiographic image of the breast of the subject in the entire radiography system according to the embodiment.

Next, the operation of the radiography system 1 according to this embodiment will be described. FIG. 4 is a flowchart illustrating an example of the flow of an imaging operation of capturing the radiographic image of the breast of the subject in the entire radiography system 1 according to this embodiment.

Figure 5:
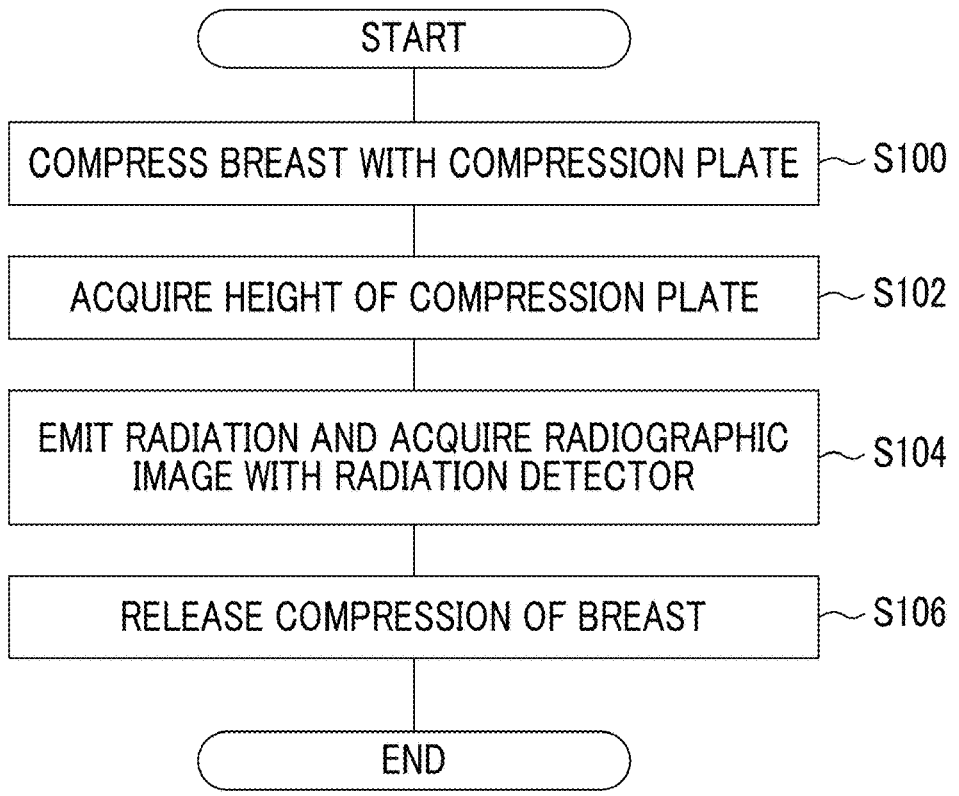
FIG. 5 is a flowchart illustrating an example of the flow of a radiography operation of the mammography apparatus according to the embodiment.

In Step S10 illustrated in FIG. 4, the mammography apparatus 10 performs the CC imaging in response to a command input from the user through the console 6. In a case in which the user positions the subject, the mammography apparatus 10 starts a radiography operation in response to a command from the user. FIG. 5 is a flowchart illustrating an example of the flow of the radiography operation in the mammography apparatus 10 according to this embodiment.

In Step S100 illustrated in FIG. 5, the control unit 30 compresses the breast placed on the imaging surface 24 of the imaging table 16 with the compression plate 20.

In a case in which the breast is compressed and fixed by the compression plate 20, in Step S102, the control unit 30 acquires the height of the compression plate 20, specifically, the distance between the imaging surface 24 and the compression plate 20. A method for acquiring the height of the compression plate 20 in the control unit 30 is not particularly limited. For example, the control unit may detect the amount of movement of the compression plate 20 from a predetermined initial position in order to compress the breast and acquire the height of the compression plate 20 on the basis of the initial position and the amount of movement. In the radiography system 1 according to this embodiment, the height of the compression plate 20 in imaging is regarded as the thickness of the breast in imaging.

Then, in Step S104, the control unit 30 directs the radiation source 29 to irradiate the breast of the subject with the radiation X in response to a command from the user and directs the radiation detector 11 to capture the radiographic image of the breast. In addition, the image data of the radiographic image captured by the radiation detector 11 is transmitted to the console 6 in a state in which it is associated with information indicating the height of the compression plate 20 at a predetermined time, such as the time immediately after the imaging ends or the time when image data is received from the console 6.

Then, in Step S106, the control unit 30 releases the compression of the breast by the compression plate 20. Specifically, the control unit 30 moves the compression plate 20 in a direction in which the compression plate 20 becomes far away from the imaging table 16 (a direction in which the compression plate 20 becomes close to the radiation source 29) to release the compression of the breast. The radiography operation of the mammography apparatus 10 is ended by the end of this step.

In a case in which the CC imaging in Step S10 (see FIG. 4) ends in this way, in Step S12, the mammography apparatus 10 performs the MLO imaging in response to a command from the console 6. In a case in which the MLO imaging is performed following the CC imaging, in the mammography apparatus 10, the imaging unit rotating unit 19 rotates the imaging unit 12 as described above (see FIGS. 3A and 3B).

Then, in a case in which the user positions the subject, the mammography apparatus 10 performs the radiography operation to capture a radiographic image (MLO image) of the breast of the subject as described above with reference to FIG. 5.

In a case in which the mammography apparatus 10 captures the CC image and the MLO image in this way, in Step S14, the console 6 performs a mammary gland percentage derivation process, whose example will be described with reference to FIG. 6, to derive the percentage of the mammary glands of the breast from the radiographic image. Then, the imaging operation in the entire radiography system 1 ends.

As such, the console 6 according to this embodiment has a function of deriving the percentage of the mammary glands of the breast from the radiographic image of the breast. Here, the principle of deriving the percentage of the mammary glands of the breast from the radiographic image will be described. The percentage of the mammary glands means the volume ratio of the mammary gland tissues to the breast tissues. The percentage of the mammary glands indicates the percentage of the mammary glands in a thickness direction of the breast which is the emission direction of the radiation X. In a case in which there are no mammary glands and only fat is present, the percentage of the mammary glands is 0. As the density of the mammary glands becomes higher, the percentage of the mammary glands becomes higher.

Figure 7:
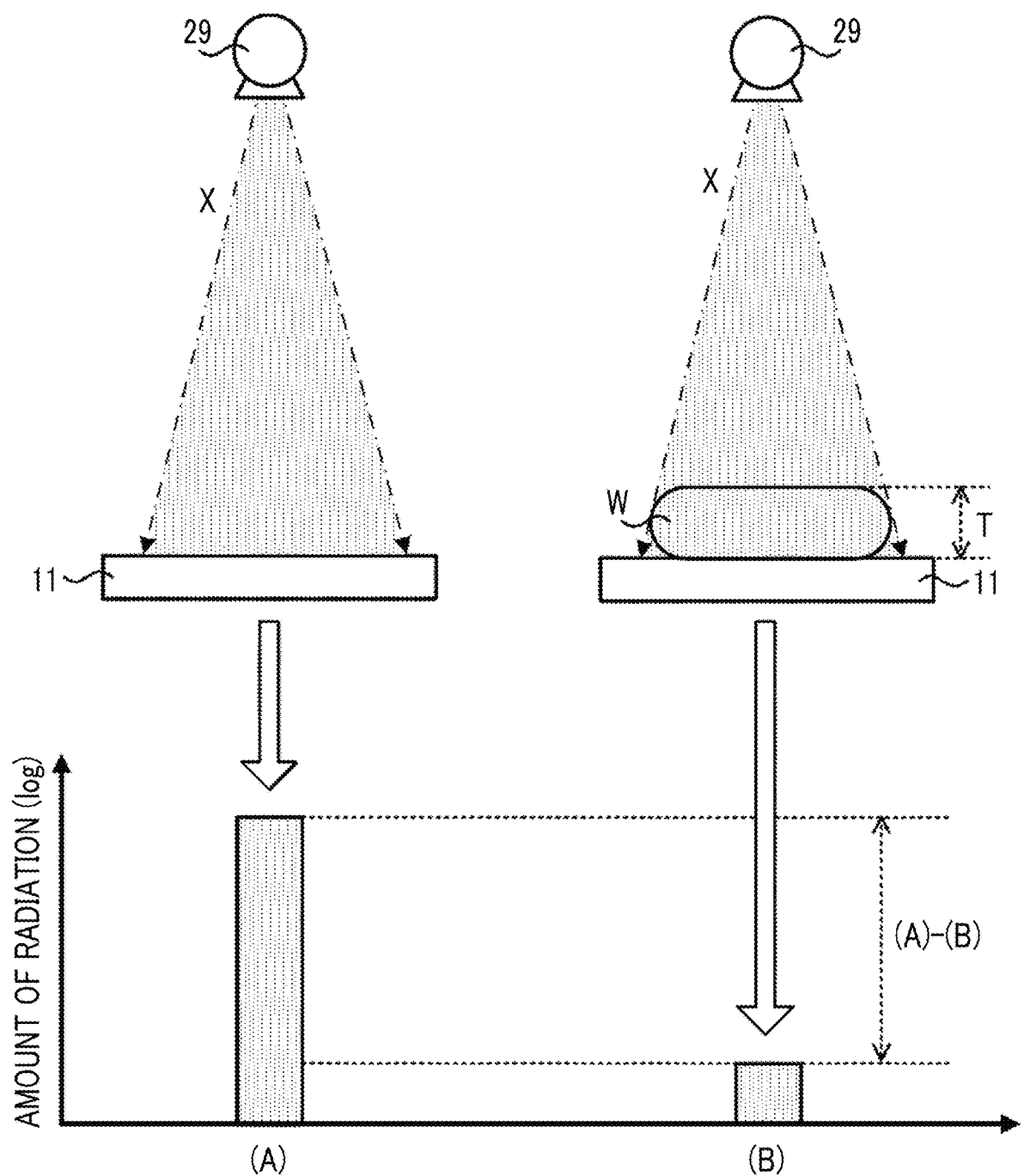
FIG. 7 is a diagram schematically illustrating the principle of deriving the percentage of the mammary glands.

As illustrated in FIG. 7, since the radiation X passes through the breast which is an object W and is attenuated, the amount of radiation reaching the radiation detector 11 (hereinafter, referred to as "the amount of incident radiation") varies. In FIG. 7, (A) schematically illustrates a case in which the radiation X emitted from the radiation source 29 directly reaches the radiation detector 11 without passing through the breast and (B) schematically illustrates a case in which the radiation X emitted from the radiation source 29 passes through the breast and reaches the radiation detector 11. A difference ((A)−(B)) between the amount of incident radiation in the case of (A) and the amount of incident radiation in the case of (B) is equal to the attenuation of the radiation X by the breast. The attenuation of the radiation X by the breast is determined by the thickness T of the breast and the composition (the percentage R of the mammary glands) of the breast. In a case in which the tissues of the breast include the mammary gland tissues and fat tissues, specifically, the attenuation ((A)−(B)) by the breast is derived by the following Expression (1). In the following Expression (1), R indicates the percentage (a numerical value in the range of 0 to 1) of the mammary glands.

$$(A)-(B) = \bar{\mu}_a \times (1-R) \times T + \bar{\mu}_g \times R \times T \quad (1)$$

$\bar{\mu}_a$: an attenuation coefficient of the fat tissue
$\bar{\mu}_g$: an attenuation coefficient of the mammary gland tissue In the above-mentioned Expression (1), $\bar{\mu}_a \times (1-R) \times T$ indicates the attenuation of the radiation X by the fat tissues.

In addition, $\bar{\mu}_g \times R \times T$ indicates the attenuation of the radiation X by the mammary gland tissues.

The percentage R of the mammary glands is derived for each pixel of the radiographic image (breast image) by the following Expression (2) from the above-mentioned Expression (1).

$$R = \frac{\log I_0 - \log I_1 - \bar{\mu}_a \times T}{(\bar{\mu}_g - \bar{\mu}_a) \times T} \quad (2)$$

In the above-mentioned Expression (2), $I_0$ is the amount of incident radiation on a direct region (so-called directly irradiated region) corresponding to the radiation X that is directly emitted without passing through the breast in the radiographic image and $I_1$ is the amount of incident radiation on a breast region.

The percentage R of the mammary glands derived for each pixel by the above-mentioned Expression (2) is integrated in the entire breast image (breast region) of the radiographic image to derive the volume of the mammary glands in the entire breast and the percentage of the mammary glands with respect to the volume of the entire breast.

For example, the method disclosed in JP2010-253245A is known as the method for deriving the percentage of the mammary glands for each pixel of the breast image. In the method disclosed in JP2010-253245A, a fat image A obtained in a case in which it is assumed that the entire breast is composed of only the fat tissues is estimated in order to derive the percentage of the mammary glands from only information obtained from the radiographic image. Since the following Expression (3) is obtained for the fat image A, the percentage of the mammary glands is derived by the following Expression (4) obtained by removing the thickness T of the breast from the above-mentioned Expression (2) using the following Expression (3).

$$\log A = \log I_0 - \bar{\mu}_a \times T \qquad (3)$$

$$R = \frac{\log A - \log I_1}{\log I_0 - \log A} \times \frac{1}{\bar{\mu}_g/\bar{\mu}_a - 1} \qquad (4)$$

The above-mentioned method uses the values of the fat tissue pixels obtained by a portion of the breast which is estimated to be composed of only the fat tissues from the breast image of the radiographic image of the breast. However, in some cases, the fat tissue pixel is not included in the breast image. For the type of breast, a fatty type, a mammary gland scattered type, a non-uniform high-concentration type, and a high-concentration type are generally known, which are described in the mammary gland density classification of the mammographic quality control manual. Among these types, in the non-uniform high-concentration type and the high-concentration type into which the breast with a relatively high mammary gland density is classified, that is, in a so-called dense breast, the fat tissue pixels have a higher tendency not to be included in the breast image than those in other types. In a case in which the fat tissue pixel is not included in the breast image and the above-mentioned method is applied, there is a concern that the accuracy of deriving the percentage of the mammary glands will be reduced.

Figure 8:
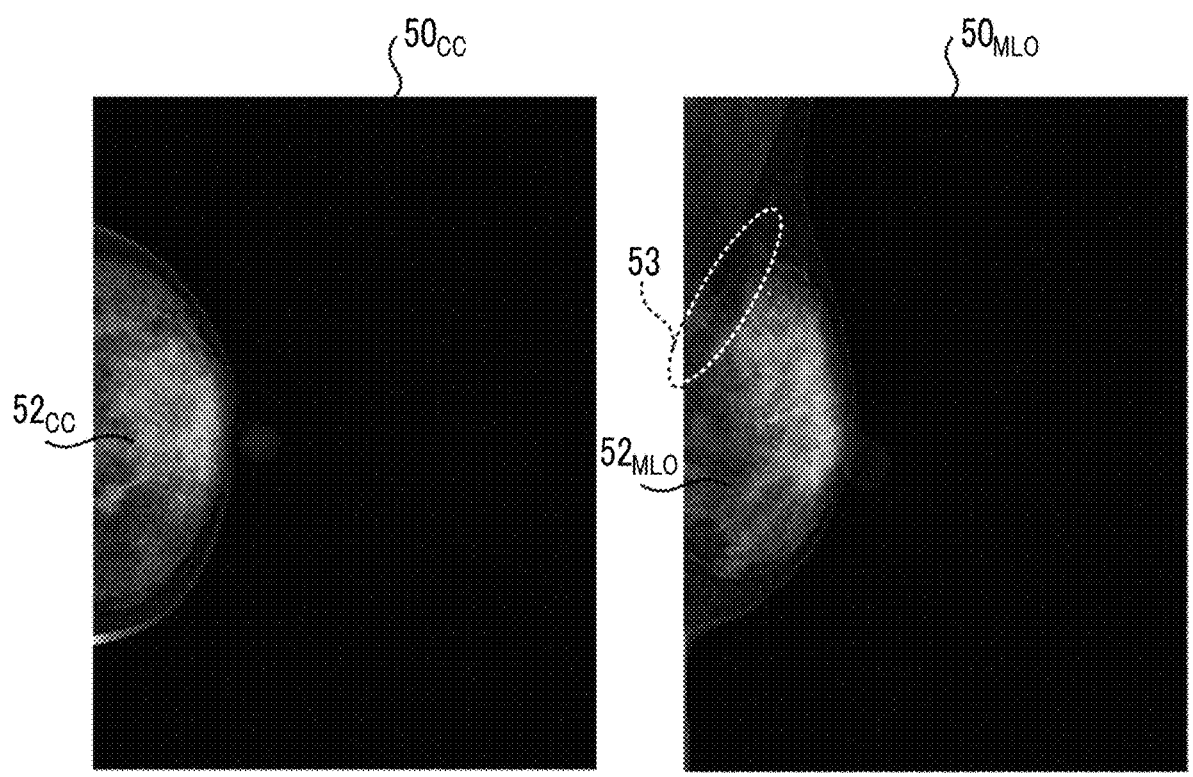
FIG. 8 is a diagram illustrating an example of a CC image and an MLO image.

Of the CC image and the MLO image, in the CC image, the fat tissue pixels have a higher tendency not to be included in the breast image than those in the MLO image. The method for compressing the breast varies depending on the type of imaging as described above with reference to FIGS. 3A and 3B. Therefore, as illustrated in FIG. 8, the appearances of the breast, that is, a breast image $52_{CC}$ and a breast image $52_{MLO}$ are different in a CC image $50_{CC}$ and an MLO image $50_{MLO}$. For example, in the high-concentration-type breast, in many cases, the mammary gland tissues are included in the breast image $52_{CC}$ of the CC image $50_{CC}$ as a whole. In contrast, in many cases, the fat tissues are included in a portion in the vicinity of a boundary 53 between the breast and the pectoralis major in the breast image $52_{MLO}$ of the MLO image $50_{MLO}$.

Therefore, in a case in which the fat tissue pixel is not included in the breast image of the CC image, the console 6 according to this embodiment derives the percentage of the mammary glands in the CC image using the analysis result of the MLO image. Then, the console 6 according to this embodiment converts the value of the fat tissue pixel included in the breast image of the MLO image into the value of the fat tissue pixel estimated to be included in the CC image. Specifically, the console 6 converts the value $A_{MLO}$ of the fat tissue pixel included in the breast image of the MLO image into the value $A_{CC}$ of the fat tissue pixel estimated to be included in the CC image, using the following Expression (5).

$$\log A_{CC} = \log A_{MLO} + \frac{I_{0CC}}{I_{0MLO}} - \bar{\mu}_a(T_{CC} - T_{MLO}) \qquad (5)$$

In the above-mentioned Expression (5), $I0_{CC}$ is the amount of incident radiation on the direct region of the CC image, $I0_{MLO}$ is the amount of incident radiation on the direct region of the MLO image, $T_{CC}$ is the thickness of the breast in the CC imaging, and $T_{MLO}$ is the thickness of the breast in the MLO imaging.

In the above-mentioned Expression (5), conversion is performed using the thickness of the breast. An error in the thickness of the breast acquired in imaging varies depending on, for example, the type of the compression plate 20, the thickness of the compression plate 20, and compression force. However, in a case in which the breast is the same, for example, the type of the compression plate 20, the thickness of the compression plate 20, and compression force may be the same in the CC imaging and the MLO imaging. An error in the thickness of the breast in the CC imaging is considered to be equal to an error in the thickness of the breast in the MLO imaging. Therefore, it is considered that the difference between the thickness $T_{CC}$ of the breast and the thickness $T_{MLO}$ of the breast in the above-mentioned Expression (5) does not include an error and is close to a true value.

Next, the mammary gland percentage derivation process performed by the console 6 will be described with reference to FIG. 6. FIG. 6 is a flowchart illustrating an example of the flow of the mammary gland percentage derivation process performed by the control unit 40 of the console 6 according to this embodiment. In addition, for example, in the mammary gland percentage derivation process according to this embodiment, the high-concentration-type breast is used as the breast with a relatively high mammary gland density.

Figure 6:
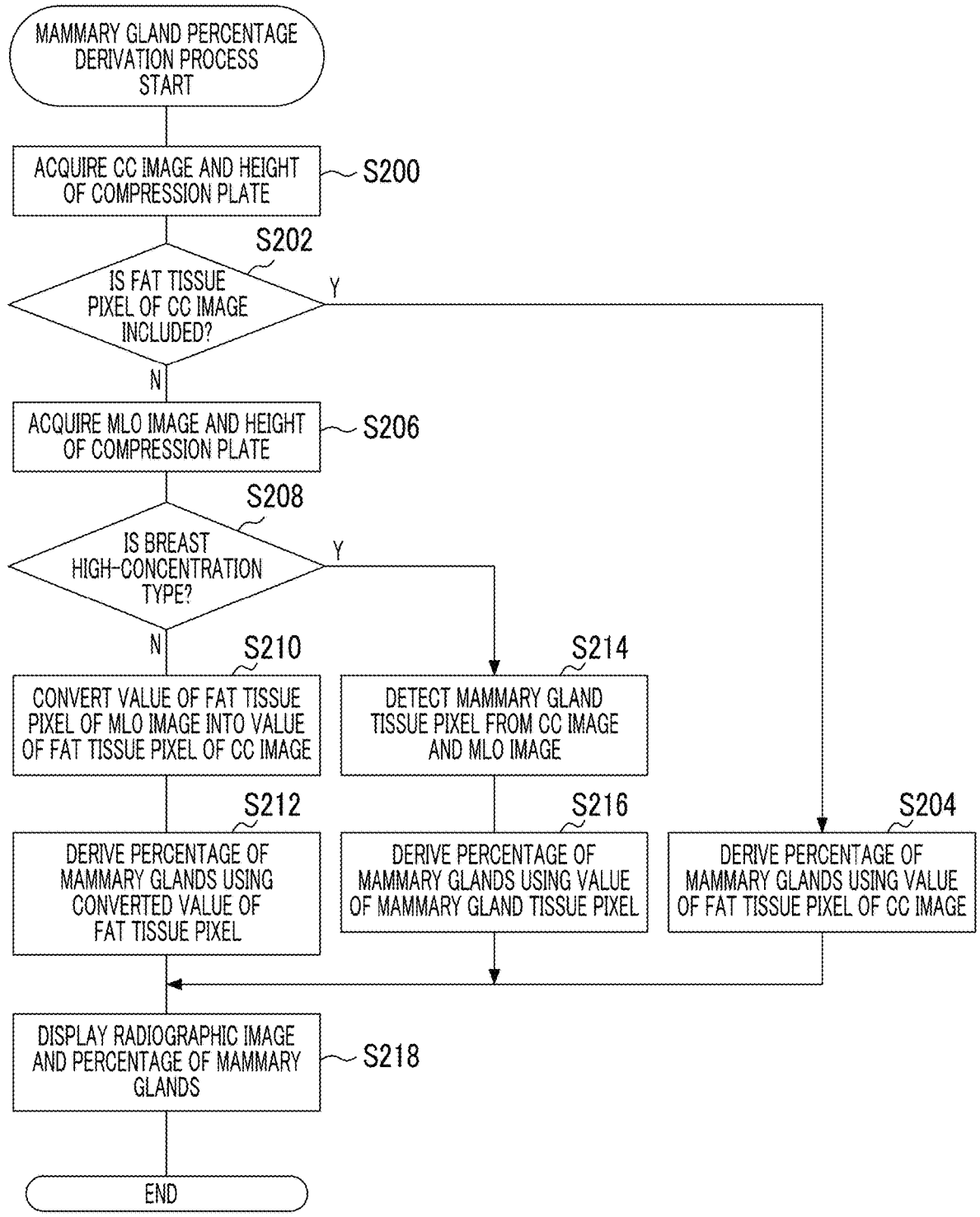
FIG. 6 is a flowchart illustrating an example of the flow of a mammary gland percentage derivation process performed by the console according to the embodiment.

For example, in a case in which the mammography apparatus 10 ends the MLO imaging (Step S12 in FIG. 4), in the console 6 according to this embodiment, the CPU 40A of the control unit 40 executes a mammary gland percentage derivation processing program stored in the ROM 40B to perform the mammary gland percentage derivation process illustrated in FIG. 6. In a case in which the mammary gland percentage derivation process is performed, the control unit 40 functions as an example of an acquisition unit, a derivation unit, and a determination unit according to the present disclosure.

As illustrated in FIG. 6, in Step S200, the control unit 40 acquires the CC image and the height of the compression plate 20. Specifically, the control unit 40 acquires image data of the CC image and the height of the compression plate 20 associated with the image data of the CC image. In addition, the acquisition destination of the CC image is not particularly limited as long as it is, for example, a device in which a desired CC image is stored and may be, for example, any one of the mammography apparatus 10 or the storage unit 42 of the host apparatus.

Then, in Step S202, the control unit 40 determines whether the fat tissue pixel is included in the breast image of the CC image. The term "fat tissue pixel" is a pixel corresponding to a portion of the breast which is estimated to be composed of only the fat tissues. For example, the "fat tissue pixel" may be a pixel corresponding to a portion of the breast in which the percentage of the fat tissues is higher than that of at least the mammary gland tissues and is greater than a predetermined threshold value for regarding a portion of the breast as being composed of only the fat tissues.

In a case in which the fat tissue pixel is included in the breast image, the determination result in Step S202 is "Yes" and the control unit 40 proceeds to Step S204. In Step S204, the control unit 40 derives the percentage R of the mammary glands on the basis of the value of the fat tissue pixel in the CC image, using the above-mentioned Expression (4), and proceeds to Step S218. In this embodiment, the percentage of the mammary glands in the entire breast is derived. However, the invention is not limited to this embodiment. For example, the percentage of the mammary glands may be derived in a portion, such as a portion in which the density of the mammary glands seems to be high or a portion in which the density of the mammary glands seems to be low.

On the other hand, in a case in which no fat tissue pixels are included in the breast image of the CC image, the determination result in Step S202 is "No" and the control unit 40 proceeds to Step S206. In Step S206, the control unit 40 acquires the MLO image and the height of the compression plate 20. Specifically, the control unit 40 acquires image data of the MLO image and the height of the compression plate 20 associated with the image data of the MLO image. In addition, the acquisition destination of the MLO image is not particularly limited as in Step S200.

Then, in Step S208, the control unit 40 determines whether the type of breast is the high-concentration type. A method for determining whether the type of breast is the high-concentration type in the control unit 40 is not particularly limited. For example, a method may be used which detects a breast region and a skin line from a breast image, calculates a first index value indicating the degree of a single composition of the breast region, detects the boundary between the fat tissues and the mammary gland tissues in a predetermined range from the skin line to the breast region in the breast image, calculates a second index value indicating the degree of the clogging of the mammary glands with respect to the breast region on the basis of at least one of the strength of the boundary or the distance from the skin line, and identifies the type of breast on the basis of the first index value and the second index value.

In a case in which the type of breast is not the high-concentration type, the determination result in Step S208 is "No" and the control unit 40 proceeds to Step S210. In this case, since the breast is not a so-called dense breast, the fat tissue pixel is included in the breast image of the MLO image.

Then, in Step S210, the control unit 40 converts the value of the fat tissue pixel in the MLO image into the value of the fat tissue pixel in the CC image using the above-mentioned Expression (5).

Then, in Step S212, the control unit 40 derives the percentage of the mammary glands using the value of the fat tissue pixel in the CC image converted in Step S210 as described above and proceeds to Step S218.

In contrast, in a case in which the type of breast is the high-concentration type, the determination result in Step S208 is "Yes" and the control unit 40 proceeds to Step S214. In this case, since the breast is a so-called dense breast, the possibility that the fat tissue pixel will not be included in the breast images of both the MLO image and the CC image is high.

Then, in Step S214, the control unit 40 detects the mammary gland tissue pixel included in the breast image of at least one of the CC image or the MLO image. As described above, in the case of the so-called dense breast, the mammary gland tissue pixels obtained by a portion of the breast which is estimated to be composed of only the mammary gland tissues are included in the breast image. The term "mammary gland tissue pixel" is a pixel corresponding to a portion of the breast which is estimated to be composed of only the mammary gland tissues. For example, the "mammary gland tissue pixel" may be a pixel corresponding to a portion of the breast in which the percentage of the mammary gland tissues is higher than that of at least the fat tissues and is greater than a predetermined threshold value for regarding a portion of the breast as being composed of only the mammary gland tissues. In addition, whether to use the CC image or the MLO image may be predetermined or may be selected by the user.

Then, in Step S216, the control unit 40 derives the percentage of the mammary glands using the value of the mammary gland tissue pixel detected in Step S214 and proceeds to Step S218. A method for deriving the percentage of the mammary glands from the value of the mammary gland tissue pixel in the control unit 40 is not particularly limited. For example, the percentage R of the mammary glands may be derived using the following Expression (6) in a case in which the value of the mammary gland tissue pixel is G.

$$R = 1 - \frac{\log G - \log I_1}{(\overline{\mu}_a - \overline{\mu}_g) \times T} \tag{6}$$

In a case in which the value G of the mammary gland tissue pixel detected from the MLO image is used, the control unit 40 applies an expression obtained by replacing "A" and "a" in the above-mentioned Expression (6) with "G" and "g" to convert the value G of the mammary gland tissue pixel of the MLO image into the value of the mammary gland tissue pixel of the CC image and then derives the percentage of the mammary glands.

In Step S218, the control unit 40 displays the radiographic image and the derived percentage of the mammary glands on the display unit 46 and ends the mammary gland percentage derivation process. In addition, the radiographic image displayed on the display unit 46 by the control unit 40 is not particularly limited. It is preferable to display at least the CC image.

As described above, in the console 6 according to this embodiment, the control unit 40 functions as an acquisition unit that acquires a CC image and an MLO image as a plurality of radiographic images of the same breast which have been captured in a plurality of different states related to the compression of the breast and a derivation unit that derives, on the basis of the amount of incident radiation derived from the value of a fat tissue pixel in a radiographic image in which the fat tissue pixel obtained by a portion of the breast which is estimated to be composed of only the fat tissues is included in a breast image among the plurality of radiographic images acquired by the acquisition unit, the percentage of the mammary glands of a breast image in a radiographic image different from the radiographic image used to derive the amount of incident radiation.

As such, in the console 6 according to this embodiment, in a case in which the fat tissue pixel obtained by a portion of the breast which is estimated to be composed of only the fat tissues is not included in the radiographic image of the breast, the percentage of the mammary glands in the breast image is derived using the fat tissue pixels in the radiographic images of the same breast which are captured under different conditions related to compression.

Therefore, according to the console 6 of this embodiment, even in a case in which the fat tissue pixel obtained by a portion of the breast which is estimated to be composed of only the fat tissues is not included in the radiographic image of the breast, it is possible to derive the percentage of the mammary glands with high accuracy.

In this embodiment, the aspect in which the plurality of radiographic images captured in a plurality of different states related to the compression of the breast are the CC image and the MLO image has been described above. However, the invention is not limited to this embodiment. The plurality of radiographic images may include radiographic images including different fat tissue pixels. For example, in a case in which the positioning of the subject is changed, the state related to the compression of the breast is changed. Therefore, a plurality of radiographic images in which the positions of the subject are different from each other may be used.

Figure 9:
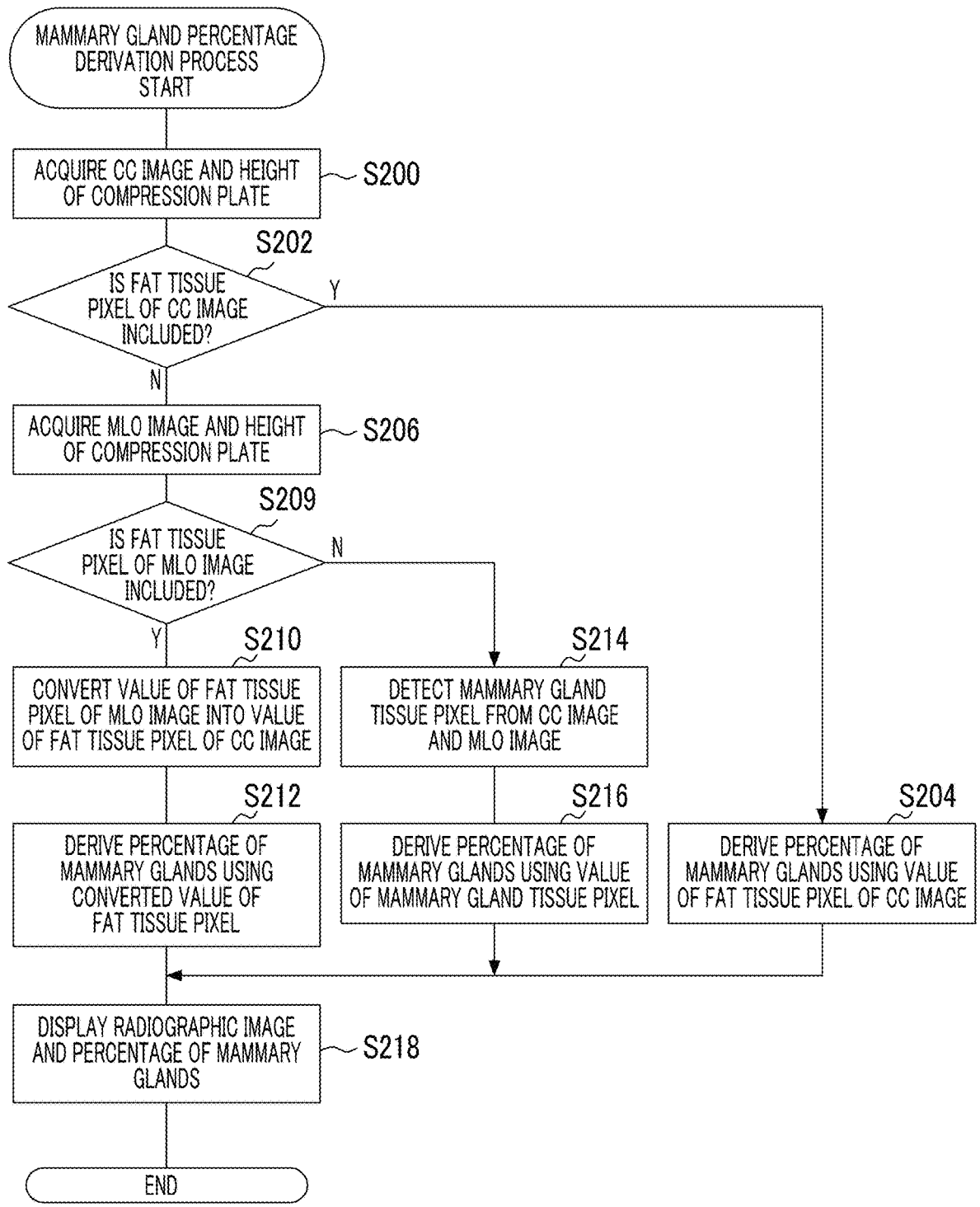
FIG. 9 is a flowchart illustrating another example of the flow of the mammary gland percentage derivation process performed by the console according to the embodiment.

In the mammary gland percentage derivation process performed by the console 6 according to this embodiment, in a case in which the breast is determined to be a dense breast (in the case of Y in Step S208 of FIG. 6), the value of the mammary gland tissue pixel is used to derive the percentage of the mammary glands. However, the following aspect may be used. Instead of the determination in Step S208, as in Step S209 in another example of the mammary gland percentage derivation process illustrated in FIG. 9, it is determined whether the fat tissue pixel is included in the breast image of the MLO image. In a case in which the fat tissue pixel is not included in the breast image, the determination result is "No" and the process proceeds to Step S214. In a case in which the fat tissue pixel is included in the breast image, the determination result is "Yes" and the process proceeds to Step S210.

In this embodiment, the aspect in which the value of the fat tissue pixel of the MLO image is converted into the value of the fat tissue pixel of the CC image by the above-mentioned Expression (5) has been described above. However, the aspect of the conversion is not limited to the aspect using the above-mentioned Expression (5).

In a case in which the percentage of the mammary glands is derived using the MLO image, the control unit 40 of the console 6 may further derive the percentage of the mammary glands in the MLO image, using the value of the fat tissue pixel (or the mammary gland tissue pixel) of the MLO image, and may display both the percentage of the mammary glands in the MLO image and the percentage of the mammary glands in the CC image on the display unit 46.

In the above-described embodiment, the aspect in which the high-concentration-type breast is used as the breast with a relatively high mammary gland density has been described. What kind of breast the breast with a relatively high mammary gland density is not limited to the above-described embodiment. For example, one of the non-uniform high-concentration-type breast and the high-concentration-type breast may be used as the breast with a relatively high mammary gland density. In addition, for example, the breasts corresponding to classification by the United States Breast Imaging Reporting and Data System (BI-RADS) evaluation system may be used. In BI-RADS, the breasts are classified into any of four categories (a to d) according to the density of the mammary glands. However, the breasts classified into category d or categories c and d may be used as the breast with a relatively high mammary gland density. In addition, the breast defined as a so-called dense breast may be used as the breast with a relatively high mammary gland density. In addition, the specific breast defined as the dense breast may be based on predetermined criteria, such as a mammographic quality control manual and an operating system BI-RADS. Specifically, which criteria the breast with a relatively high mammary gland density is based on can vary depending on, for example, the country in which the technology of the present disclosure is operated and the standard at that time. In addition, what kind of breast the breast with a relatively high mammary gland density is and which criteria the definition of the dense breast is based on may be preset in the console 6 or may be set by the user.

In the above-described embodiment, various processors other than the CPU may perform the mammary gland percentage derivation process performed by the execution of software (program) by the CPU. In this case, examples of the processor include a programmable logic device (PLD), such as a field-programmable gate array (FPGA), whose circuit configuration can be changed after manufacture and a dedicated electric circuit, such as an application specific integrated circuit (ASIC), which is a processor having a dedicated circuit configuration designed to perform a specific process. In addition, the mammary gland percentage derivation process may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In the above-described embodiment, the aspect in which various programs, such as the programs stored in the control unit 30 of the mammography apparatus 10 and the mammary gland percentage derivation processing program stored in the control unit 40 of the console 6, are stored (installed) in the ROMs (30B and 40B) of the control unit 30 and the control unit 40 in advance has been described. However, the invention is not limited thereto. Each of the various programs may be recorded on a recording medium, such as a compact disk read only memory (CD-ROM), a digital versatile disk read only memory (DVD-ROM), or a universal serial bus (USB) memory, and then provided. In addition, each of the various programs may be downloaded from an external apparatus through the network.

In the above-described embodiment, the radiation X is not particularly limited. For example, X-rays or γ-rays may be applied.

In addition, for example, the configuration and operation of the radiography system 1, the console 6, and the mammography apparatus 10 according to the above-described embodiment are illustrative and may be changed according to the situation, without departing from the scope and spirit of the invention. In addition, the above-described embodiments may be appropriately combined with each other.

What is claimed is:

1. An image processing apparatus comprising:
   an acquisition unit, which is a processor, that acquires a first radiographic image which has been captured in a first state related to a first compression of a breast, and a second radiographic image which has been captured in a second state related to a second compression of the breast, the second state related to the second compression being different from the first state related to the first compression; and a derivation unit, which is a processor, that derives a percentage of mammary glands of a breast image in the first radiographic image on the basis of a value of a fat tissue pixel which is included in the breast image of the second radiographic image, in a case in which the breast image of the first radiographic image does not include a fat tissue pixel.

2. The image processing apparatus according to claim 1, wherein the derivation unit derives the percentage of the mammary glands for each pixel.

3. The image processing apparatus according to claim 1, wherein breast compression directions of the first state and the second state are different from each other.

4. The image processing apparatus according to claim 1, wherein the first radiographic image includes a radiographic image captured in a craniocaudal direction and the second radiographic image includes a radiographic image captured in a mediolateral-oblique direction.

5. The image processing apparatus according to claim 1, wherein the acquisition unit further acquires information indicating a thickness of each breast in the capture of the first radiographic image and the second radiographic image, and the derivation unit derives the percentage of the mammary glands on the basis of a difference between the thicknesses of the breast.

6. The image processing apparatus according to claim 1, wherein the derivation unit derives the percentage of the mammary glands on the basis of a ratio of an amount of incident radiation derived on the basis of a pixel value of a direct region corresponding to radiation which is directly emitted without passing through the breast in the second radiographic image and an amount of incident radiation derived on the basis of a pixel value of a direct region corresponding to radiation which is directly emitted without passing through the breast in the first radiographic image.

7. The image processing apparatus according to claim 1, wherein, in a case in which the breast image of the second radiographic image does not include the fat tissue pixel, the derivation unit derives the percentage of the mammary glands on the basis of a value of a mammary gland tissue pixel obtained by a portion of the breast which is estimated to be composed of only mammary gland tissues in at least one of the first radiographic image and the second radiographic image.

8. The image processing apparatus according to claim 1, further comprising:

a determination unit, which is a processor, that determines a type of the breast on the basis of the second radiographic image, wherein, in a case in which the type of the breast determined by the determination unit is a type predetermined to be a breast with a relatively high mammary gland density, the derivation unit derives the percentage of the mammary glands on the basis of a value of a mammary gland tissue pixel obtained by a portion of the breast which is estimated to be composed of only mammary gland tissues in at least one of the first radiographic image and the second radiographic image.

9. The image processing apparatus according to claim 1, wherein, the fat tissue pixel is a pixel corresponding to a portion of the breast which is estimated to be composed of only the fat tissues and includes a pixel in which the percentage of the fat tissues is greater than a predetermined threshold value of the breast.

10. The image processing apparatus according to claim 1, wherein, the derivation unit derives the percentage of the mammary glands of the breast image in the first radiographic image by converting a value of the fat tissue pixel in the first radiographic image into a value of the fat tissue pixel in the second radiographic image.

11. An image processing method comprising:

acquiring a first radiographic image which has been captured in a first state related to a first compression of a breast, and a second radiographic image which has been captured in a second state related to a second compression of the breast, the second state related to the second compression being different from the first state related to the first compression; and deriving a percentage of mammary glands of a breast image in the first radiographic image on the basis of a value of a fat tissue pixel which is included in the breast image of the second radiographic image, in a case in which the breast image of the first radiographic image does not include a fat tissue pixel.

12. A non-transitory recording medium recording an image processing program that causes a computer to perform:

acquiring a first radiographic image which has been captured in a first state related to a first compression of a breast, and a second radiographic image which has been captured in a second state related to a second compression of the breast, the second compression being different from the first compression to the same breast; and deriving a percentage of mammary glands of a breast image in the first radiographic image on the basis of a value of a fat tissue pixel which is included in the breast image of the second radiographic image, in a case in which the breast image of the first radiographic image does not include a fat tissue pixel.

* * * * *